US 8,864,668 B2

(12) United States Patent
Kim et al.

(10) Patent No.: US 8,864,668 B2
(45) Date of Patent: Oct. 21, 2014

(54) FORMATION OF AN ELASTIC IMAGE IN AN ULTRASOUND SYSTEM

(75) Inventors: Jong Sik Kim, Seoul (KR); Mok Kun Jeong, Seoul (KR)

(73) Assignee: Medison Co., Ltd., Hongchun-gun, (KR)

( * ) Notice: Subject to any disclaimer, the term of this patent is extended or adjusted under 35 U.S.C. 154(b) by 589 days.

(21) Appl. No.: 12/416,551

(22) Filed: Apr. 1, 2009

(65) Prior Publication Data

US 2009/0253987 A1 Oct. 8, 2009

(30) Foreign Application Priority Data

Apr. 2, 2008 (KR) .................. 10-2008-0030913
Apr. 2, 2008 (KR) .................. 10-2008-0030918
Apr. 2, 2008 (KR) .................. 10-2008-0030921

(51) Int. Cl.
*A61B 8/00* (2006.01)
*A61M 25/00* (2006.01)
*A61B 5/04* (2006.01)
*A61B 8/08* (2006.01)
*G01S 7/52* (2006.01)
*A61B 5/02* (2006.01)

(52) U.S. Cl.
CPC ............ *G01S 7/52046* (2013.01); *A61B 8/0833* (2013.01); *A61B 8/543* (2013.01); *G01S 7/52085* (2013.01); *A61B 8/0858* (2013.01); *A61B 5/02007* (2013.01); *G01S 7/52034* (2013.01); *G01S 7/52042* (2013.01); *A61B 8/485* (2013.01)
USPC ............ 600/438; 600/443; 600/509; 600/427

(58) Field of Classification Search
USPC ........................... 600/438, 440, 441
See application file for complete search history.

(56) References Cited

U.S. PATENT DOCUMENTS 5,615,680 A 4/1997 Sano
7,601,122 B2 * 10/2009 Zagzebski et al. ............ 600/449
(Continued)

FOREIGN PATENT DOCUMENTS

JP 5-317313 12/1993
JP 8-84729 4/1996
(Continued)

OTHER PUBLICATIONS

The Extended European Search Report issued May 3, 2012, in Application No. / Patent No. 09004659.0-2220 / 2107389.
(Continued)

*Primary Examiner* — Tse Chen
*Assistant Examiner* — Patricia Park
(74) *Attorney, Agent, or Firm* — Oblon, Spivak, McClelland, Maier & Neustadt, L.L.P.

(57) ABSTRACT

Embodiments for forming elastic images in an ultrasound system are disclosed. In one embodiment, a Tx/Rx unit repeatedly transmits/receives an ultrasound beam along scan lines in a target object to output receive signals. An image processing unit forms a plurality of consecutive ultrasound images based on the receive signals and set a center of the target object on each of the ultrasound images. The image processing unit further sets radial scan lines in radial directions with respect to the center on each of the ultrasound image and reconstructs the ultrasound images such that the radial scan lines are in parallel with each other to form reconstruction images. An elastic image forming unit forms an elastic image based on the reconstruction images.

21 Claims, 23 Drawing Sheets

(56) References Cited

U.S. PATENT DOCUMENTS

| | | | |
|---|---|---|---|
| 7,798,965 B2 * | 9/2010 | Torp et al. | 600/443 |
| 2001/0010555 A1 * | 8/2001 | Driscoll, Jr. | 348/335 |
| 2002/0072671 A1 | 6/2002 | Chenal et al. | |
| 2003/0065260 A1 * | 4/2003 | Cheng et al. | 600/427 |
| 2003/0171668 A1 * | 9/2003 | Tsujino et al. | 600/407 |
| 2004/0068184 A1 | 4/2004 | Trahey et al. | |
| 2005/0215899 A1 | 9/2005 | Trahey et al. | |
| 2006/0079772 A1 * | 4/2006 | Ichikawa et al. | 600/437 |
| 2007/0016047 A1 * | 1/2007 | Tsunoda et al. | 600/443 |
| 2008/0064956 A1 | 3/2008 | Jeong et al. | |
| 2008/0232660 A1 | 9/2008 | Hyun et al. | |
| 2010/0215225 A1 * | 8/2010 | Kadomura et al. | 382/128 |

FOREIGN PATENT DOCUMENTS

| | | | | |
|---|---|---|---|---|
| JP | 11-318884 | | 11/1999 | |
| JP | 2001-292995 | | 10/2001 | |
| JP | 2003-210460 | | 7/2003 | |
| JP | 2005-74146 | | 3/2005 | |
| JP | 2006-456 | | 1/2006 | |
| JP | 2007-195984 | | 8/2007 | |
| JP | 2008-68094 | | 3/2008 | |
| JP | 2008-237912 | | 10/2008 | |
| KR | 10-2008-0024327 | * | 3/2008 | A61B 8/00 |
| WO | WO 99/17660 | | 4/1999 | |

OTHER PUBLICATIONS

Korean Office Action issued Dec. 20, 2010, in Patent Application No. 10-2008-0030913.

Japanese Office Action, Notice of Allowance in corresponding Japanese Application JP 2009-089507, dated Dec. 10, 2013.

* cited by examiner

FORMATION OF AN ELASTIC IMAGE IN AN ULTRASOUND SYSTEM

The present application claims priority from Korean Patent Application Nos. 10-2008-0030913, 10-2008-0030918 and 10-2008-0030921 filed on Apr. 2, 2008, the entire subject matters of which are incorporated herein by reference.

TECHNICAL FIELD

The present disclosure relates to ultrasound systems, and more particularly to an ultrasound system and method for forming an elastic image.

BACKGROUND

Recently, an ultrasound system has been extensively used in the medical field due to its non-invasive and non-destructive nature. Modern high-performance ultrasound imaging systems and techniques are commonly used to produce two dimensional ultrasound images and three-dimensional ultrasound images of internal features of patients.

Generally, the ultrasound image is displayed in a Brightness-mode (B-mode) by using reflectivity caused by an acoustic impedance difference between the tissues of the target object. However, if the reflectivity of the target object is hardly different from those of the neighboring tissues such as tumor, cancer or the like, then it is not easy to recognize the target object in the B-mode image.

When the target object is a blood vessel, an intravascular ultrasound imaging method is adopted to diagnose a lipid or lesion positioned at an inside of the blood vessel. In such a case, a probe is inserted into the inside of the blood vessel to form an ultrasound image of the blood vessel. Although a high resolution of the ultrasound image of the blood vessel may be obtained through the intravascular ultrasound imaging method, there is a problem in that the blood vessel may be damaged.

SUMMARY

Embodiments for forming an elastic image in an ultrasound system are disclosed herein. In one embodiment, by way of non-limiting example, an ultrasound system comprises: a transmission/reception (Tx/Rx) unit configured to repeatedly transmit/receive an ultrasound beam along scan lines in a target object to output receive signals; an image processing unit configured to form a plurality of consecutive ultrasound images based on the receive signals and set a center of the target object on each of the ultrasound images, the image processing unit being further configured to set radial scan lines in radial directions with respect to the center on each of the ultrasound images and reconstruct the ultrasound images such that the radial scan lines are in parallel with each other to form reconstruction images; and an elastic image forming unit configured to form an elastic image based on the reconstruction images.

In another embodiment, a method of forming an elastic image in an ultrasound system including a transmission/reception (Tx/Rx) unit, an image processing unit and an elastic image forming unit, comprises: a) using the transmission/reception (Tx/Rx) unit within the ultrasound system to repeatedly transmit/receive an ultrasound beam along scan lines in a target object to output receive signals; b) using the image processing unit within the ultrasound system to form a plurality of consecutive ultrasound images based on the receive signals, set a center of the target object on each of the ultrasound images, set radial scan lines in radial directions with respect to the center on each of the ultrasound images and reconstruct the ultrasound images such that the radial scan lines are in parallel with each other to form reconstruction images; and c) using the elastic image forming unit within the ultrasound system to form an elastic image based on the reconstruction images.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

First Embodiment

Figure 1:
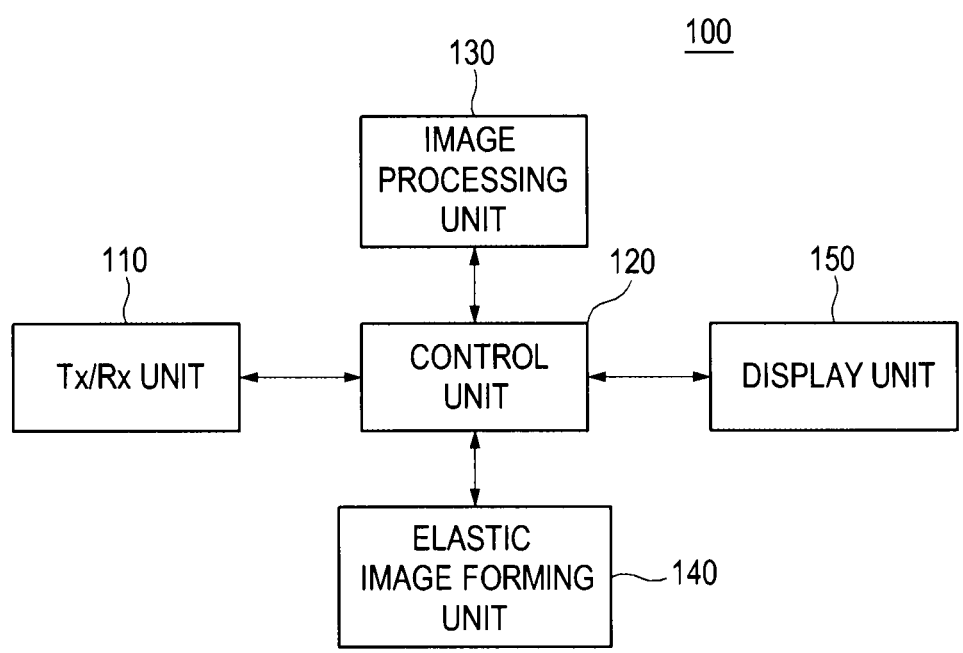
FIG. 1 is a block diagram showing an ultrasound system in accordance with a first embodiment.

Referring to FIG. 1, an ultrasound system 100 in accordance with an illustrative embodiment is shown. As depicted therein, the ultrasound system 100 may include a transmission/reception (Tx/Rx) unit 110 configured to transmit/receive an ultrasound beam to/from a target object to thereby output electrical receive signals.

The ultrasound system 100 may include a control unit 120 configured to control the Tx/Rx of the ultrasound beam in the Tx/Rx unit 110. The control unit 120 may be operable to control the Tx/Rx of the ultrasound beam to be consecutively performed in synchronization with an ECG signal provided from an electrocardiograph (not shown). Specially, the Tx/Rx of the ultrasound beam may be performed in synchronization with an ECG signal outputted when a left ventricular is in a maximum contraction and/or maximum relaxation.

Figure 2:
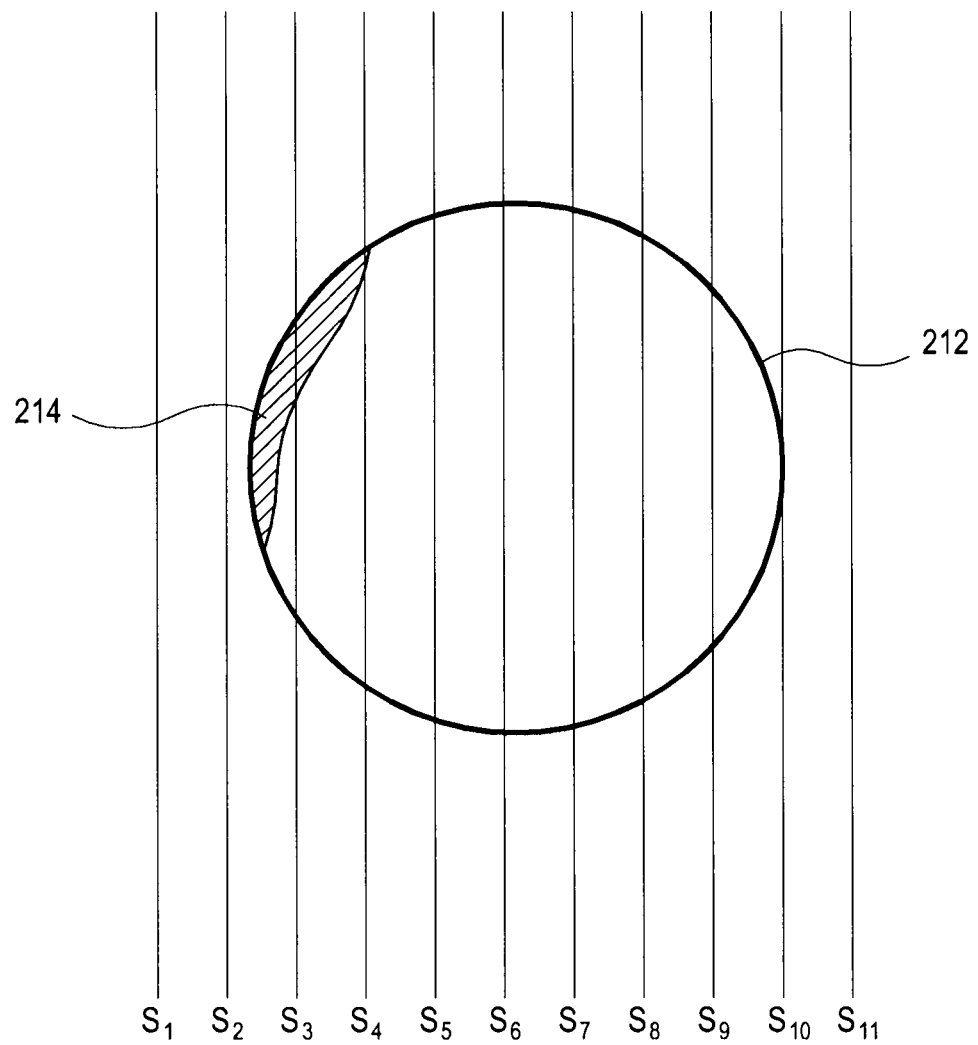
FIG. 2 is a schematic diagram illustrating scan lines in parallel with each other.
Figure 3:
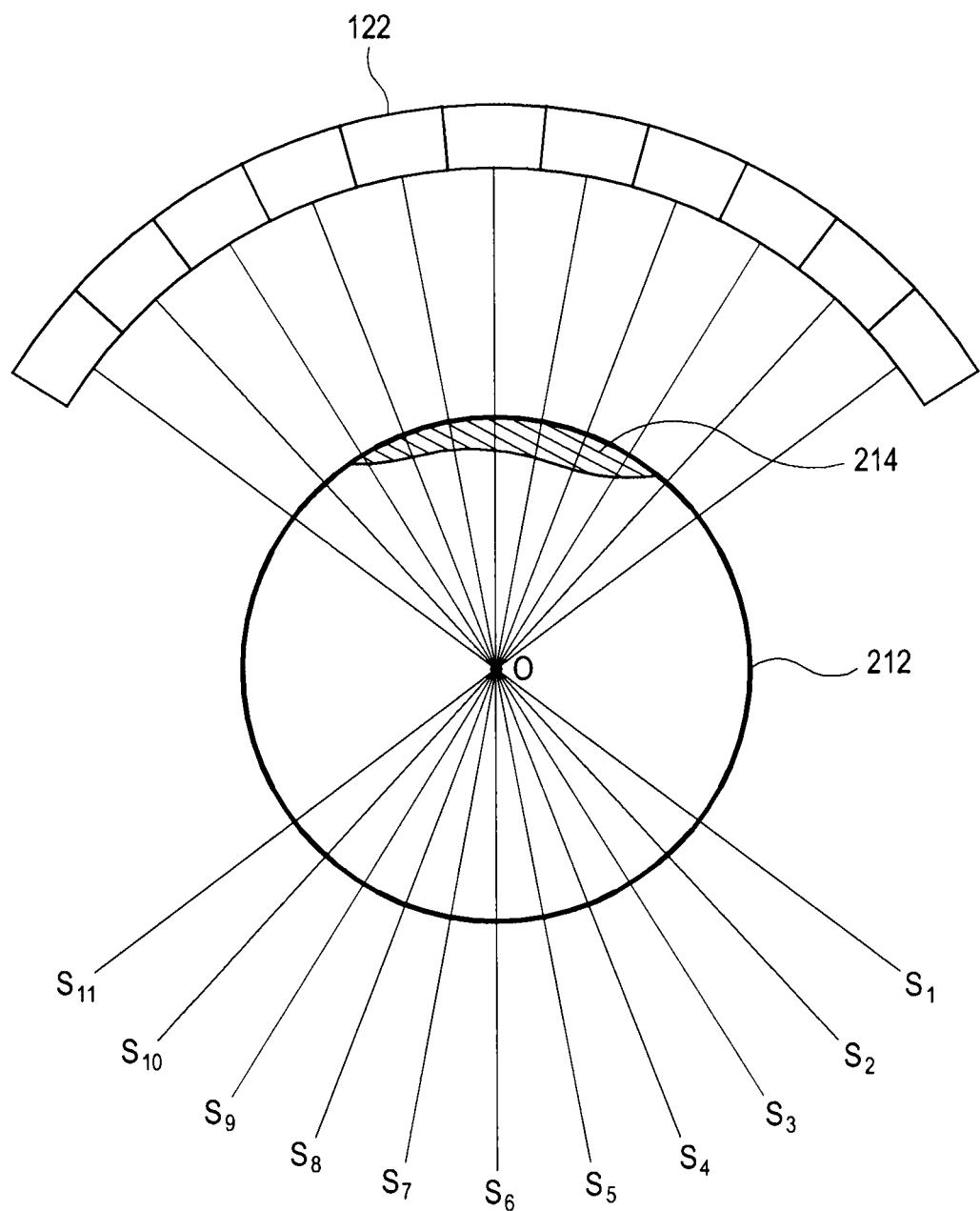
FIG. 3 is a schematic diagram illustrating scan lines converged at a specific point when a concave array transducer is adopted.

The Tx/Rx unit 110 may be operable to perform the Tx/Rx of the ultrasound beam multiple times under the control of the control unit 120. The Tx/Rx unit 110 may include a probe (not shown) containing an array transducer for generating the ultrasound beam and the electrical receive signals. In one embodiment, a linear array transducer may be adopted to generate the ultrasound beam. In such a case, the control unit 120 may set the scan lines $S_1$-$S_{11}$ to be parallel with each other, as illustrated in FIG. 2. Also, a concave array transducer 122 may be adopted to generate the ultrasound beam. In such a case, the control unit 120 may set the scan line $S_1$-$S_{11}$ to be converged at a specific point, e.g., a center of the target object, as illustrated in FIG. 3. The Tx/Rx unit 100 may further include a beam former (not shown) for performing transmit focusing and receive focusing to form a transmit beam and a receive beam. The control unit 120 may be further operable to control the entire operations of the ultrasound system 100.

The ultrasound system 100 may further include an image processing unit 130. The image processing unit 130 may be configured to consecutively form a plurality of ultrasound images by using the receive signals outputted from the Tx/Rx unit 120 under the control of the control unit 120. For the sake of convenience, a blood vessel will be referred to as an example of the target object. However, the target object may be not limited thereto.

Figure 4:
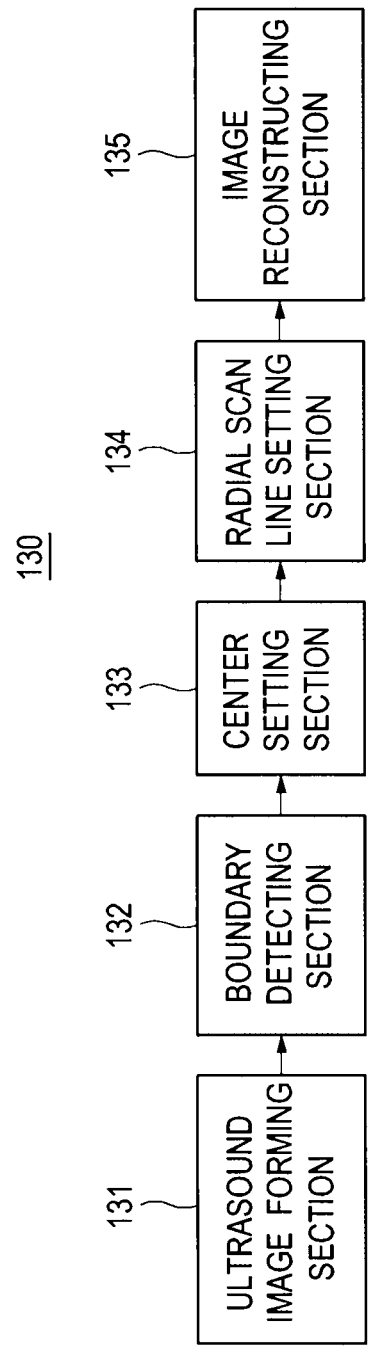
FIG. 4 is a block diagram showing an image processing unit in accordance with the first embodiment.
Figure 5:
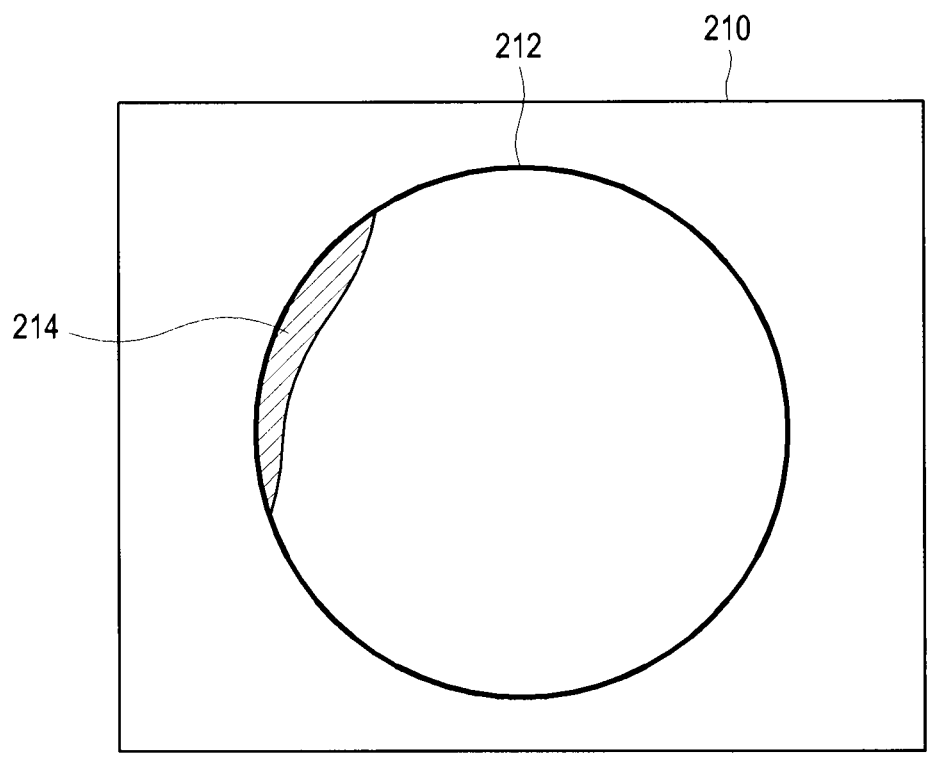
FIG. 5 is a schematic diagram showing an example of an ultrasound image.

FIG. 4 is a block diagram showing an illustrative embodiment of the image processing unit 130. Referring to FIG. 4, the image processing unit 130 may include an ultrasound image forming section 131. The ultrasound image forming section 131 may be operable to consecutively form a plurality of ultrasound images based on the receive signals. Each of the ultrasound images 210 may contain a blood vessel 212 and a lipid 214, as illustrated in FIG. 5.

The image processing unit 130 may further include a boundary detecting section 132, a center setting section 133, a radial scan line setting section 134 and an image reconstructing section 135. The boundary detecting section 132 may be operable to detect boundaries of the blood vessel on the ultrasound image 210. The boundaries may be detected based on a variation of brightness determined by using a differential operator. In one embodiment, the boundary detecting section 132 may be operable to detect the boundaries of the blood vessel 212 by using edge masks such as Sobel, Prewitt, Robert, Laplacian of Gaussian, Canny and the like. In another embodiment, the boundary detecting section 132 may be operable to detect the boundaries of the blood vessel 212 based on a difference of eigenvalues using a structure tensor.

Figure 6:
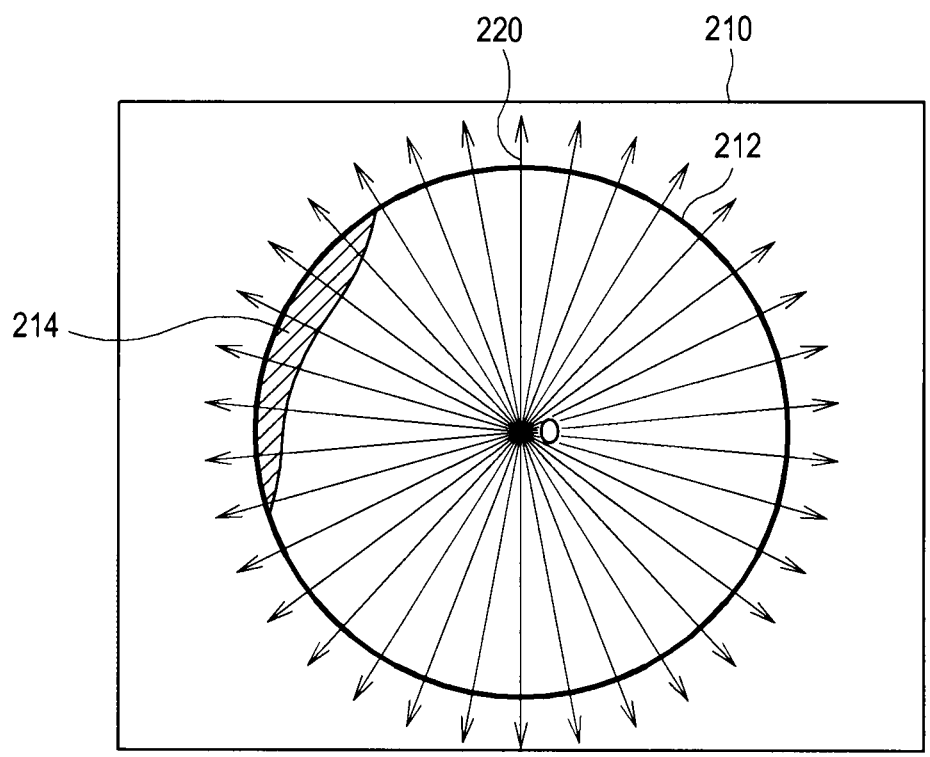
FIG. 6 is a schematic diagram showing an example of setting radial scan lines with respect to a center of a target object.

In one embodiment, the center setting section 133 may be operable to set a center "O" of the blood vessel 212 by using detected boundaries of the blood vessel 212, as illustrated in FIG. 6. Also, in another embodiment, the center of the blood vessel 212 may be set in response to a user instruction inputted through a user input unit (not shown).

The radial scan line setting section 134 may be configured to set a plurality of scan lines 220 in radial directions (hereinafter, referred to as "radial scan lines") with respect to the center "O" on the first ultrasound image 210, as illustrated in FIG. 6. The radial scan line setting section 134 may set a plurality of sample points on each of the radial scan lines 220 and acquire position information of the sampling points and image data of the sampling points based on the receive signals.

Figure 7:
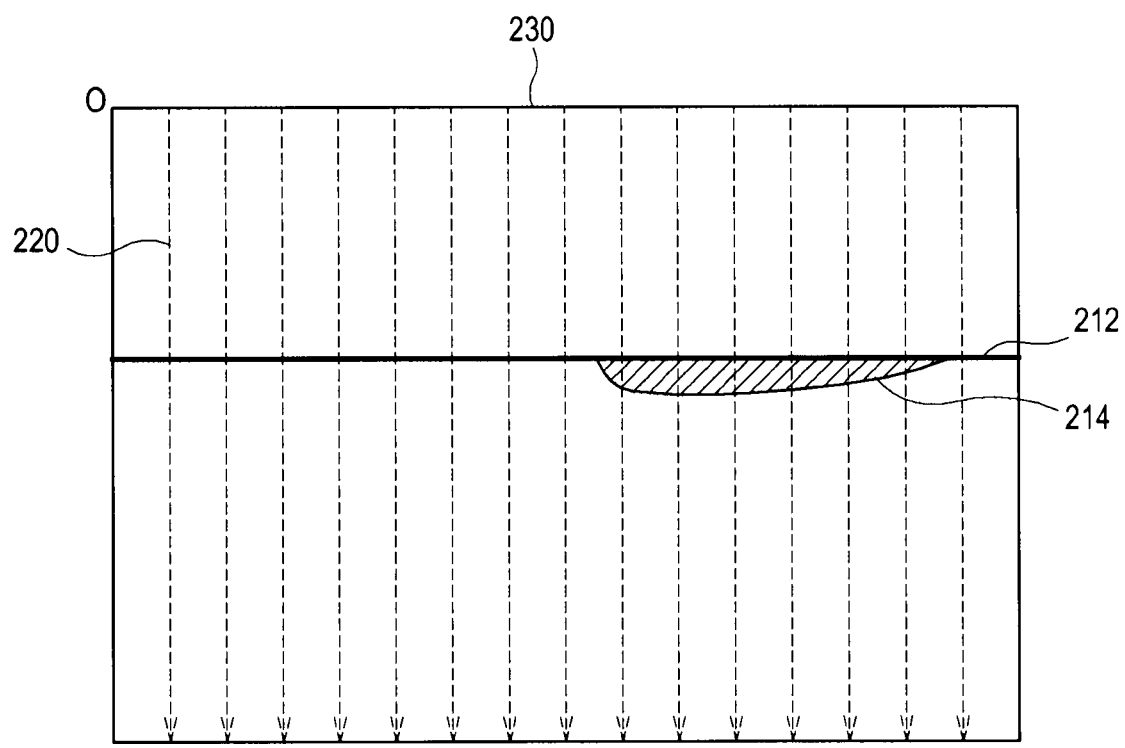
FIG. 7 is a schematic diagram showing an example of reconstructing an ultrasound image.

The image reconstructing section 135 may be operable to reconstruct the radial scan lines 220 to be parallel with each other, as illustrated in FIG. 7. The image reconstructing section 135 may be operable to form a reconstruction image corresponding to the first ultrasound image by using the reconstructed radial scan lines 220 and the image data of the sampling points on the radial scan lines. Referring again to FIG. 1, the ultrasound system 100 may further include an elastic image forming unit 140. The elastic image forming unit 140 may be operable to perform auto correlation upon an $n^{th}$ reconstruction image and an $(n+1)^{th}$ reconstruction image to thereby compute an elastic modulus, wherein n is an integer equal to or greater than 1. The elastic image forming unit 140 may be further operable to form an elastic image based on the computed elastic modulus. That is, the elastic image forming unit 140 may compute the elastic modulus corresponding to displacement of the blood vessel, the lipid and neighboring tissues caused by contraction and relaxation of the blood vessel, and then form the elastic image based on the computed elasticity modulus.

A display unit 150 may be one of a liquid crystal display, a cathode ray tube, a plate panel display and the like capable of displaying the elastic image formed in the elastic image forming unit 140. However, the display unit 150 may not be limited thereto. Also, the first ultrasound image and the second image may be displayed on the display unit 150.

Second Embodiment

Figure 8:
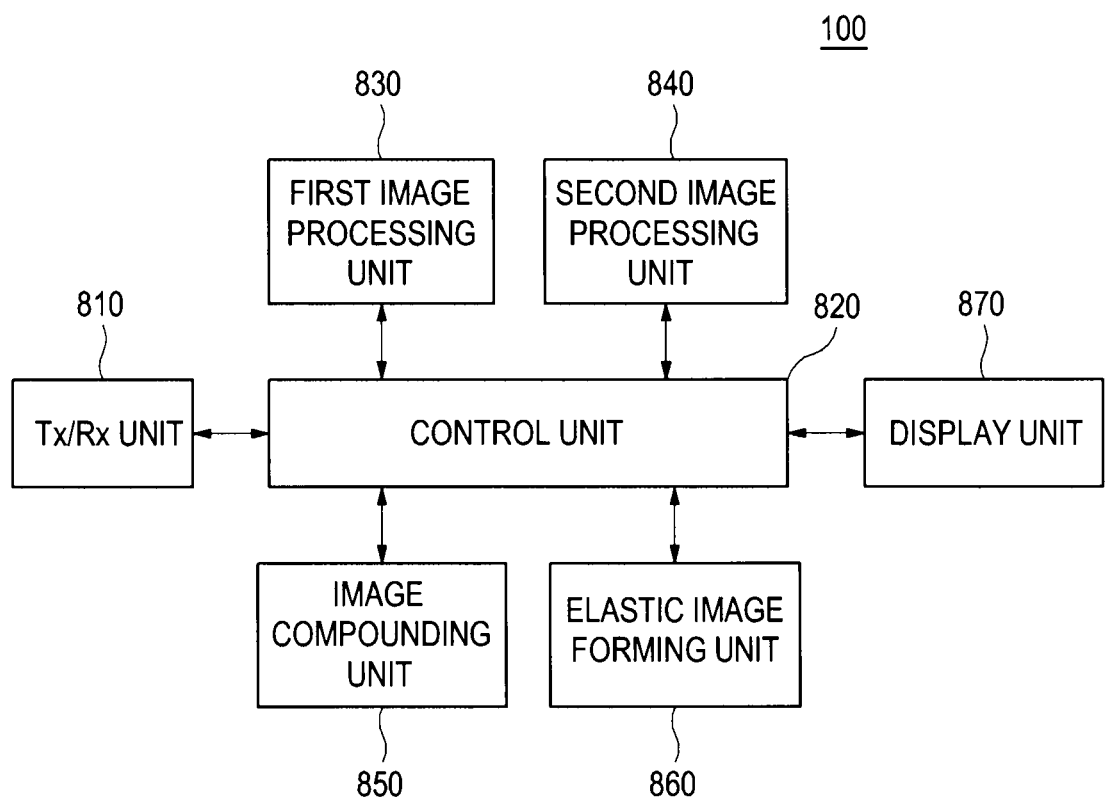
FIG. 8 is a block diagram showing an ultrasound system in accordance with a second embodiment.

FIG. 8 is a block diagram showing an illustrative embodiment of an ultrasound system. As depicted in FIG. 8, the ultrasound system 800 may further include an image compounding unit 850 compared to the ultrasound system 100 of FIG. 1. Also, the ultrasound system 800 may include a first image processing unit 830 and a second image processing unit 840.

The ultrasound system 800 may include a Tx/Rx unit 810. The Tx/Rx unit 810 may include a probe (not shown) for transmitting an ultrasound beam along scan lines in a target object and receive ultrasound echoes reflected from the target object to thereby output electrical receive signals. For the sake of convenience, a blood vessel will be referred to as an example of the target object. The probe may include a linear array transducer containing a plurality of elements. The Tx/Rx unit 810 may further include a beam former for performing transmit focusing and receive focusing.

Figure 9:
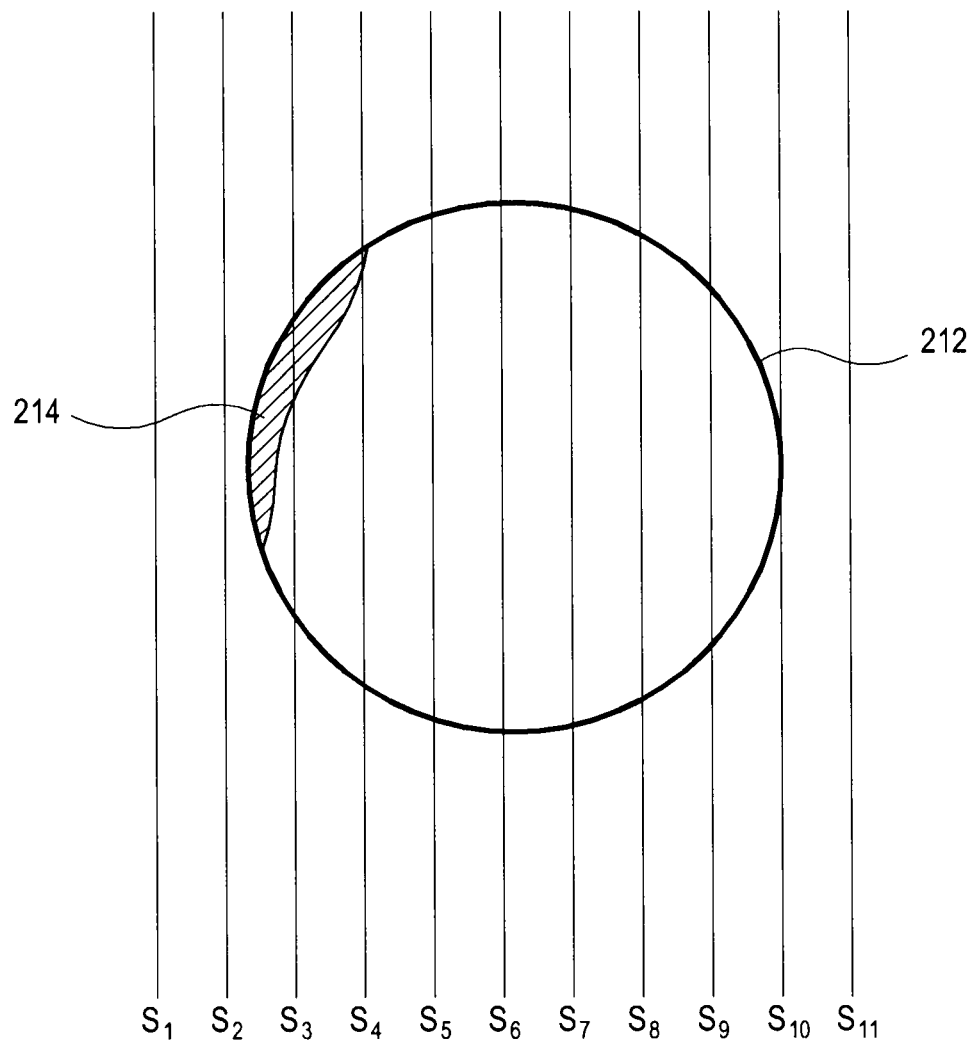
FIG. 9 is a schematic diagram illustrating normal scan lines.

The ultrasound system 800 may further include a control unit 820 operable to control the Tx/Rx of the ultrasound beam. The control unit 820 may be operable to set scan lines $S_1$-$S_{11}$ ("normal scan lines") in the normal directions to a linear array transducer (not shown) in the probe, as illustrated in FIG. 9. The control unit 820 may be operable to control the ultrasound beam to be scanned along the normal scan lines.

Figure 10:
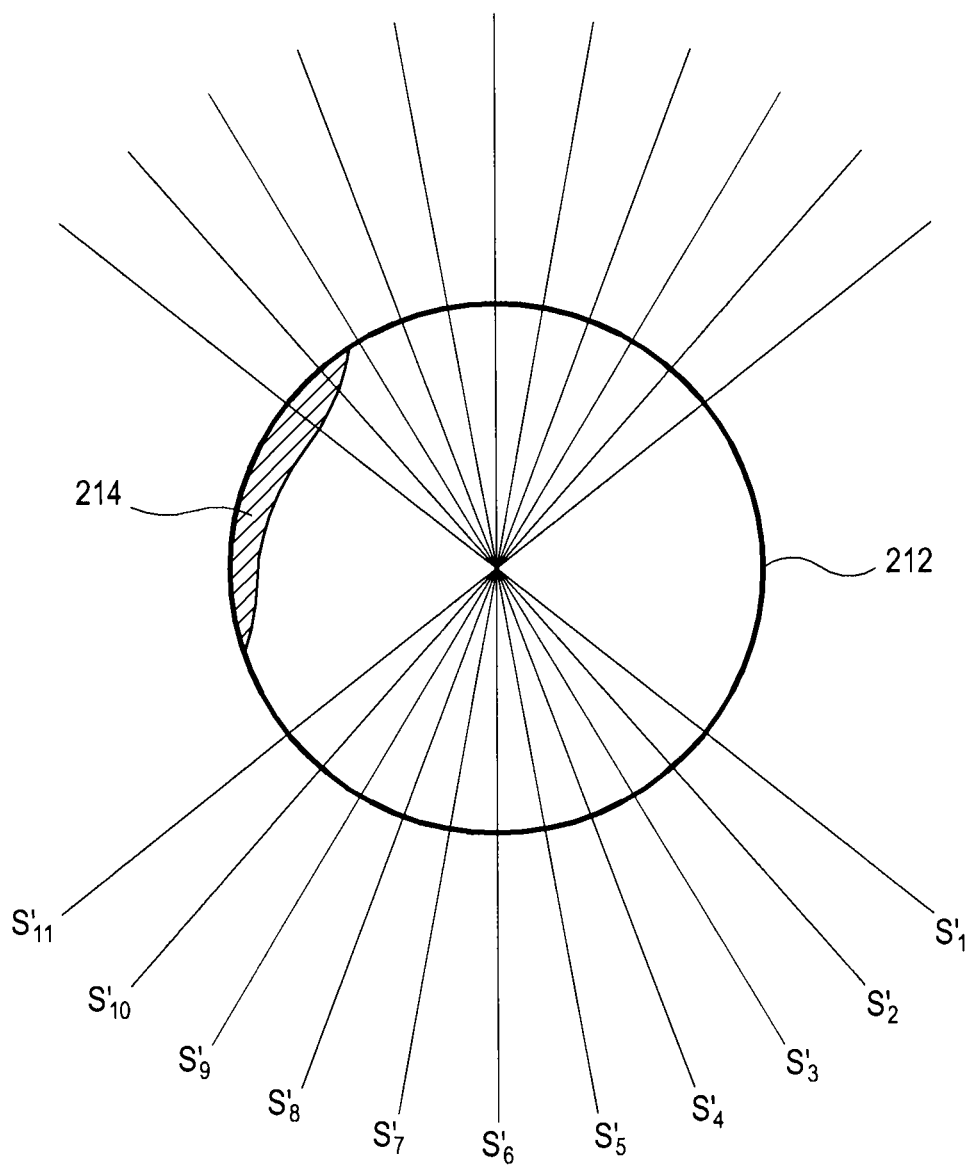
FIG. 10 is a schematic diagram illustrating steered scan lines.

Also, the control unit 820 may be configured to set the scan lines $S'_1$-$S'_{11}$ to be steered ("steered scan lines"), as illustrated in FIG. 10. The control unit 820 may be operable to control the Tx/Rx unit 810 such that the ultrasound beam is transmitted along the scan lines. Detailed description for setting the steered scan lines $S'_1$-$S'_{11}$ will be described later. The Tx/Rx unit 810 may output first electrical receive signals obtained by scanning the normal scan lines and second electrical receive signals obtained by scanning the steered scan lines. In one embodiment, the scanning of the normal scan lines and the steered scan lines may be alternately carried out.

Figure 11:
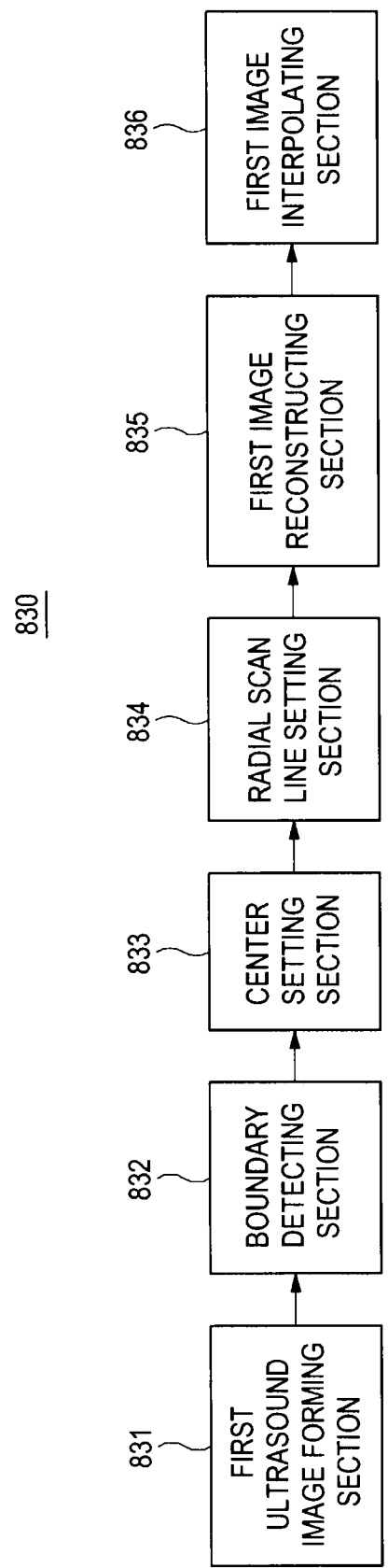
FIG. 11 is a block diagram showing a first image processing unit in accordance with the second embodiment.
Figure 12:
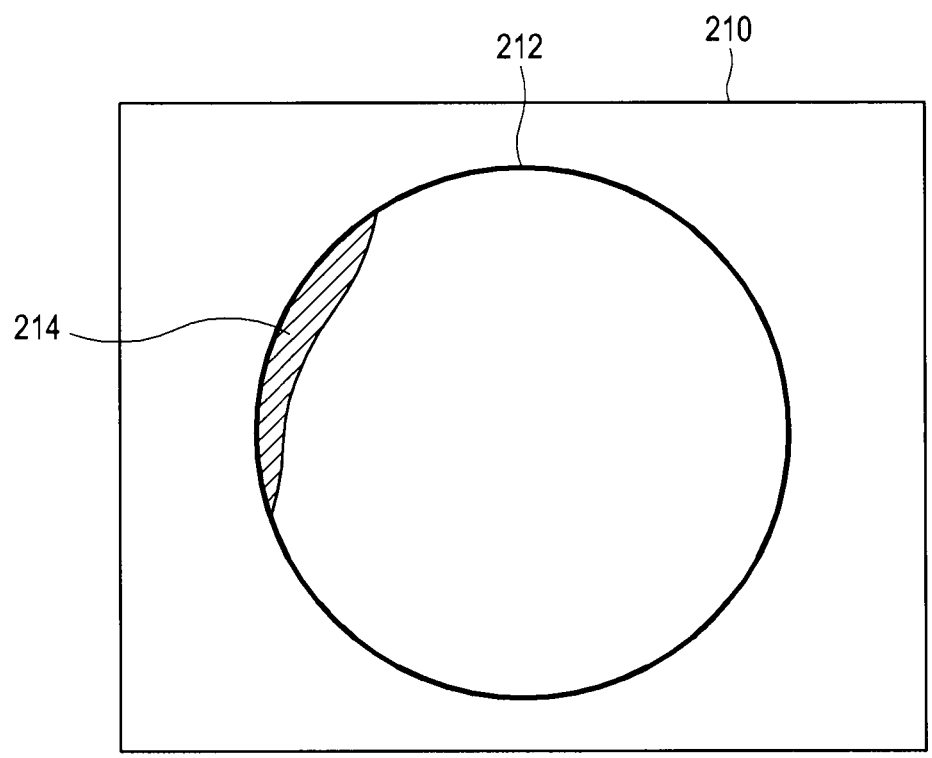
FIG. 12 is a schematic diagram showing an example of an ultrasound image formed by scanning normal scan lines.

The ultrasound system 800 may include a first image processing 830 that may receive the first receive signals. Referring to FIG. 11, the first image processing unit 830 may include a first ultrasound image forming section 831. The first ultrasound image forming section 831 may be operable to form a first ultrasound image 210 based on the first receive signals, as illustrated in FIG. 12.

The first processing unit 830 may further include a boundary detecting section 832, which is configured to detect boundaries of a blood vessel 212 on the first ultrasound image 210. The boundaries may be detected based on the variation of brightness determined by using a differential operator. In one embodiment, the boundary detecting section 832 may be operable to detect the boundaries of the blood vessel 212 by using edge masks such as Sobel, Prewitt, Robert, Laplacian of Gaussian, Canny and the like. In another embodiment, the boundary detecting section 832 may be operable to detect the boundaries of the blood vessel 212 based on a difference of eigen values using a structure tensor.

Figure 13:
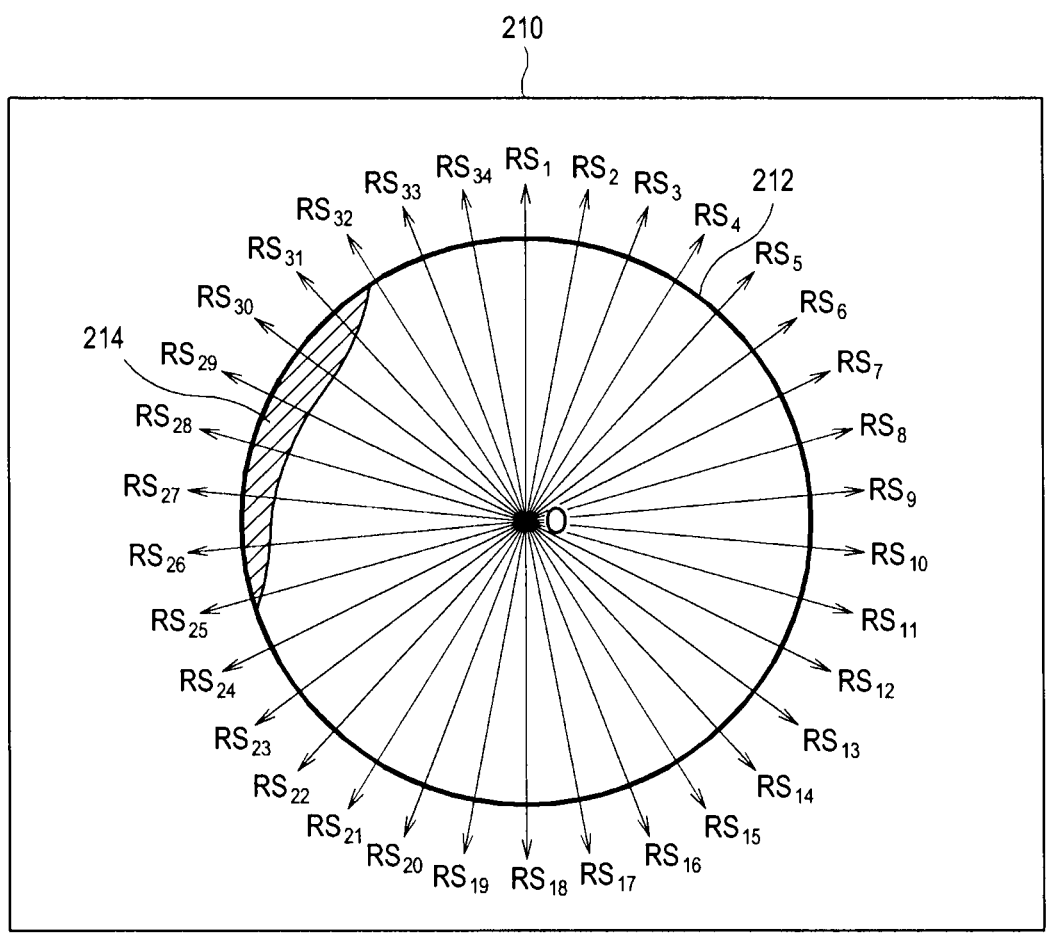
FIG. 13 is a schematic diagram showing an example of setting radial scan lines on an ultrasound image.
Figure 14:
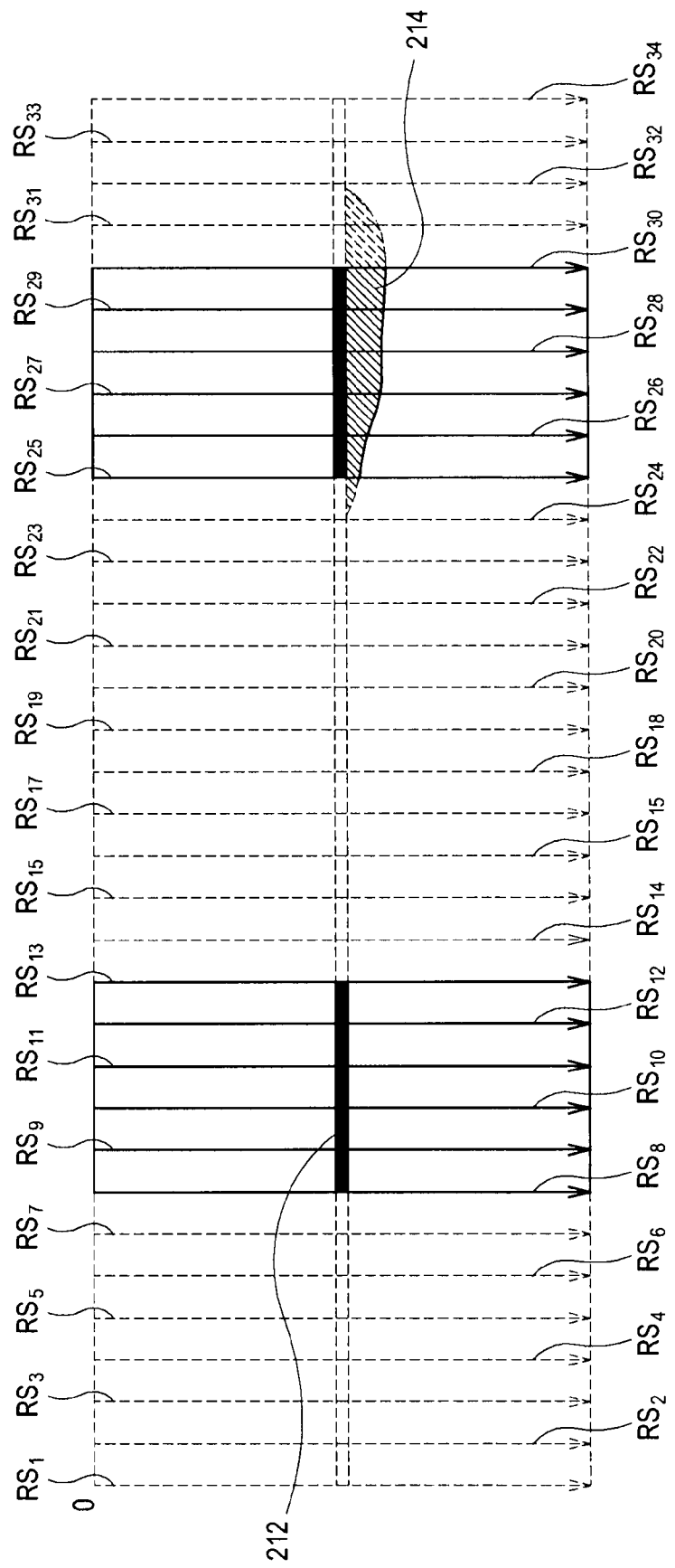
FIG. 14 is a schematic diagram showing an example of reconstructing an ultrasound image by using radial scan lines in a first image processing unit in accordance with the second embodiment.

The first image processing unit 830 may further include a center setting section 833. In one embodiment, the center setting section 833 may be operable to set a center "O" of the blood vessel 212 by using detected boundaries of the blood vessel 212, as illustrated in FIG. 13. However, the center setting of the blood vessel 212 is not limited thereto. In another embodiment, the center of the blood vessel 212 may be set in response to a user instruction inputted through a user input unit (not shown).

The first image processing unit 830 may further include a radial scan line setting section 834. The radial scan line setting section 134 may be operable to set a plurality of scan lines $RS_1$-$RS_{34}$ in radial directions (hereinafter, referred to as "radial scan lines") with respect to the center on the first ultrasound image 210, as illustrated in FIG. 13. The number of radial scan lines may be determined according to an interval of the radial scan lines, i.e., a steered angle, which may be set by the control unit 820. The radial scan line setting section 834 may set a plurality of sample points on each of the radial scan lines $RS_1$-$RS_{34}$ and acquire position information of the sampling points and image data at the sampling points based on the first receive signals.

The image processing unit 830 may further include a first image reconstructing section 835. The first image reconstructing section 835 may be operable to reconstruct the radial scan lines $RS_1$-$RS_{34}$ to be in parallel with each other. The first image reconstructing section 835 may be operable to form a first reconstruction image corresponding to the first ultrasound image by using the reconstructed radial scan lines $RS_1$-$RS_{34}$ and the image data of the sampling points on the radial scan lines. In one embodiment, the first image reconstructing section 135 may be operable to form the first reconstruction image 230 by using the image data corresponding to the radial scan lines $RS_8$-$RS_{13}$ and $RS_{25}$-$RS_{30}$, which are not overlapped with the steered scan lines $S'_1$-$S'11$ shown in FIG. 10. The radial scan lines $RS_8$-$RS_{13}$ and $RS_{25}$-$RS_{30}$ may be determined based on the property of the array transducer and the center of the blood vessel.

Figure 15:
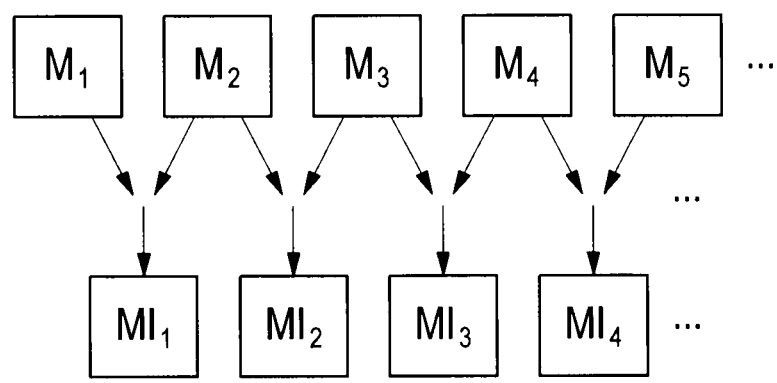
FIG. 15 is a schematic diagram showing an example of interpolating reconstruction images in a first image processing unit in accordance with the second embodiment.

The image processing unit 830 may further include a first image interpolating section 836. The first image interpolating section 836 may be operable to interpolate two consecutive first reconstruction images to thereby form a first interpolation image. As illustrated in FIG. 15, the first image processing unit 830 may be configured to perform interpolation upon the first reconstruction image $M_1$ and the first reconstruction image $M_2$ to thereby form the first interpolation image $MI_1$. Also, the first image processing unit 830 may be operable to perform interpolation upon the first reconstruction image $M_2$ and the first reconstruction image $M_3$ to thereby form the first interpolation image $MI_2$. Similar to the above, a plurality of the first interpolation images $MI_3$, $MI_4$ . . . may be formed through the interpolation of the first reconstruction images.

Referring back to FIG. 8, the control unit 820 may be further operable to set the steered scan lines $S'_1$-$S'_{11}$, which are illustrated in FIG. 8, based on the center information of the blood vessel. That is, the control unit 820 may be operable to set the steered scan lines $S'_1$-$S'_{11}$ to be converged at the center of the blood vessel. The control unit 820 may control the Tx/Rx unit 810 such that the ultrasound beam is transmitted along the steered scan lines $S'_1$-$S'_{11}$. In such a case, the electrical receive signal outputted from the Tx/Rx unit 810 will be referred to as "second receive signals."

Figure 16:
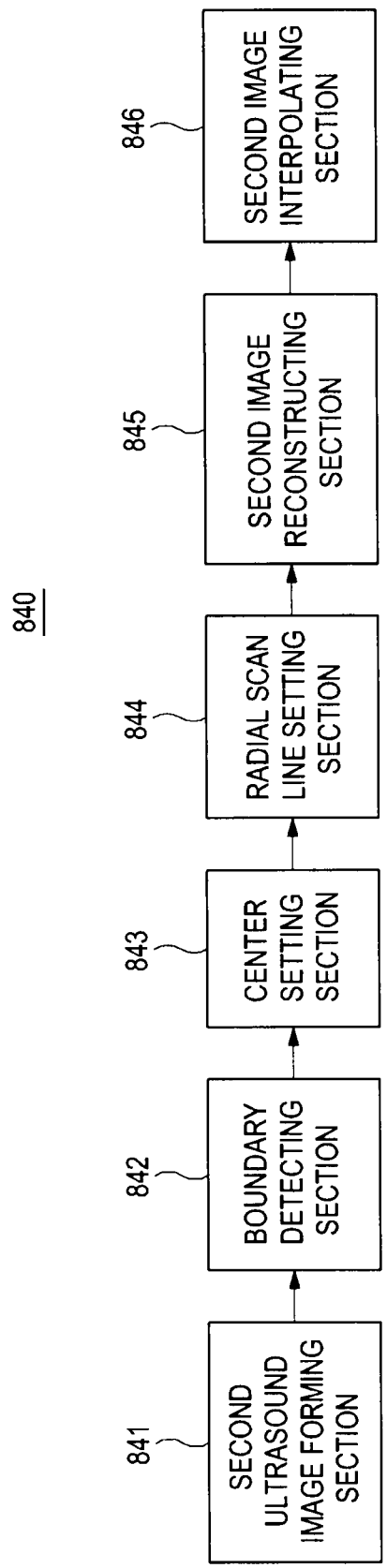
FIG. 16 is a block diagram showing a second image processing unit in accordance with the second embodiment.

The ultrasound system 800 may further include a second image processing unit 840, which may receive the second receive signals. Referring to FIG. 16, the second image processing unit 840 may include a second ultrasound image forming section 841 that may receive the second receive signals. The second ultrasound image forming section 841 may be operable to form a second ultrasound image based on the second receive signals.

The second image processing unit 840 may further includes a boundary detecting section 842 that may be operable to detect boundaries of the blood vessel in the same manner of the boundary detection in the boundary detecting section 832 of the first image processing unit 830.

The second image processing unit 840 may further include a center setting section 843. In one embodiment, the center setting section 843 may be operable to set a center of the blood vessel based on the center set by the center setting section 833 of the first image processing unit 830.

The second image processing unit 840 may further include a radial scan line setting section 844. The radial scan line setting section 844 may be operable to set a plurality of scan lines $RS_1$-$RS_{34}$ in radial directions (hereinafter, referred to as "radial scan lines") with respect to the center of the blood vessel, as illustrated in FIG. 13. The number of the radial scan lines may be determined according to an interval of the radial scan lines, i.e., a steering angle, which may be set by the control unit 820. In one embodiment, the steering angle of the radial scan lines $RS_1$-$RS_{34}$ may be set to be equal to a steering angle of the steered scan lines $S'_1$-$S'_{11}$ shown in FIG. 10. The radial scan line setting unit 844 may set the radial scan lines $RS_1$-$RS_7$, $RS_{14}$-$RS_{24}$ and $RS_{31}$-$RS_{34}$, which are matched with the steered scan lines $S'_1$-$S'_{11}$. The radial scan line setting section 844 may set a plurality of sample points on each of the radial scan lines and acquire position information of the sampling points and image data at the sampling points based on the second receive signals.

Figure 17:
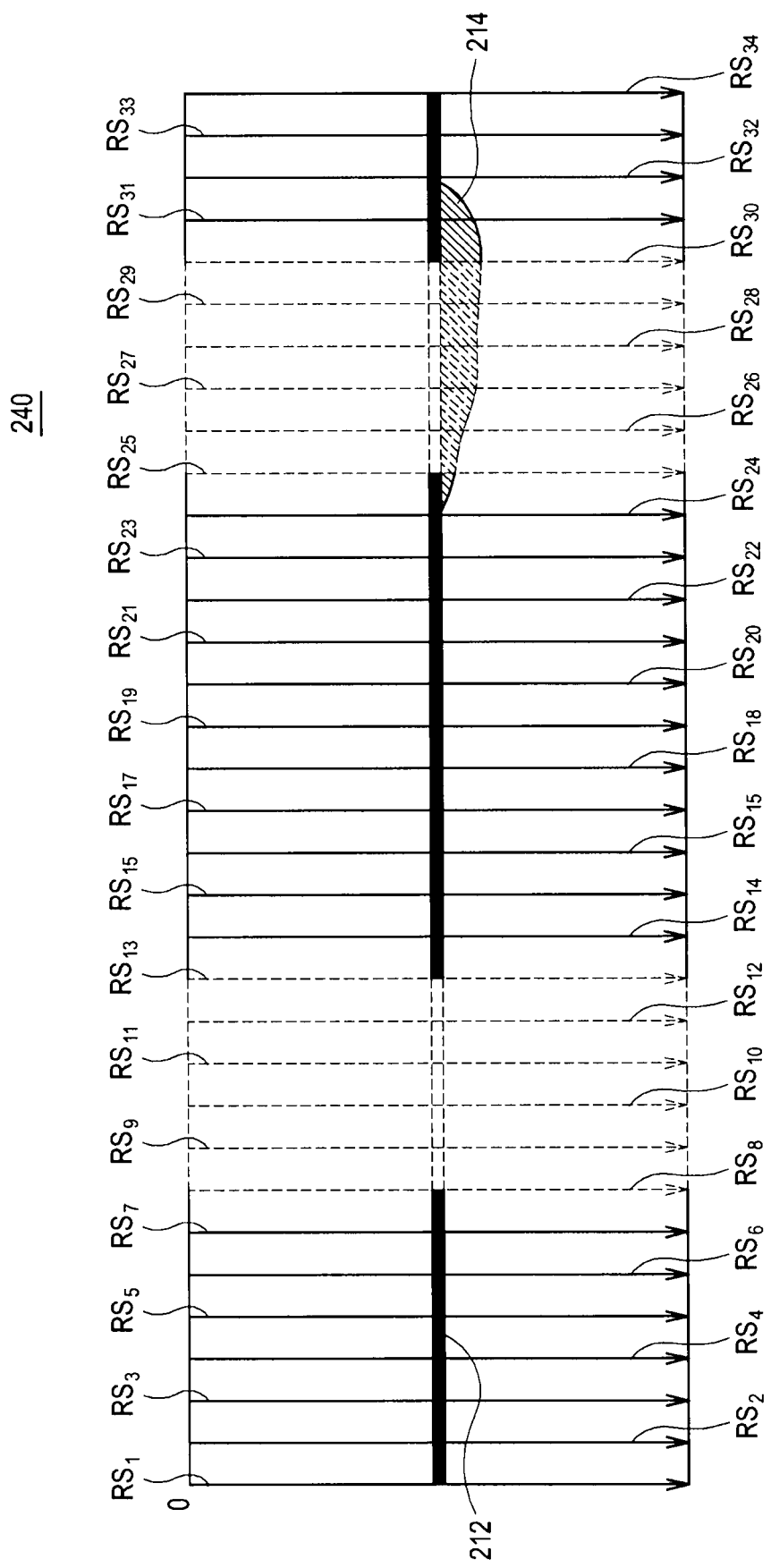
FIG. 17 is a schematic diagram showing an example of reconstructing an ultrasound image by using radial scan lines in a second image processing unit in accordance with the second embodiment.

The image processing unit 840 may further include a second image reconstructing section 845. The second image reconstructing section 845 may be operable to reconstruct the radial scan lines $RS_1$-$RS_{34}$ to be in parallel with each other, as illustrated in FIG. 17. The second image reconstructing section 845 may be further operable to form a second reconstruction image corresponding to the second ultrasound image by using the reconstructed radial scan lines $RS_1$-$RS_{34}$ and the image data of the sampling points on the radial scan lines. In one embodiment, the second image reconstructing section 845 may be operable to form the second reconstruction image 240 by using the image data corresponding to the radial scan lines $RS_1$-$RS_7$, $RS_{14}$-$RS_{24}$ and $RS_{31}$-$RS_{34}$.

Figure 18:
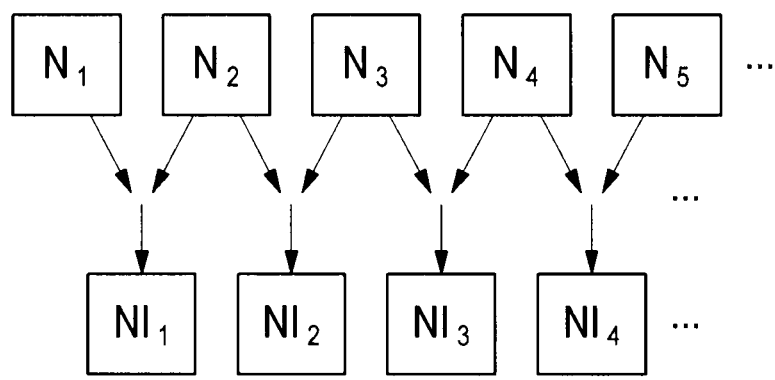
FIG. 18 is a schematic diagram showing an example of interpolating reconstruction images in a second image processing unit in accordance with the second embodiment.

The second image processing unit 840 may further include a second image interpolating section 846. The second image interpolating section 846 may be configured to interpolate two consecutive second reconstruction images to form a second interpolation image. As illustrated in FIG. 18, the second image interpolating section 846 may be operable to perform the interpolation upon the second reconstruction image $N_1$ and the second reconstruction image $N_2$ to thereby form the second interpolation image $NI_1$. Also, the second image interpolating section 846 may be operable to perform the interpolation upon the second reconstruction image $N_2$ and the second reconstruction image $N_3$ to thereby form the second interpolation image $NI_2$. In the same manner as above, the second interpolation images $NI_3$, $NI_4$ . . . may be formed through the interpolation of the second reconstruction images.

Figure 19:
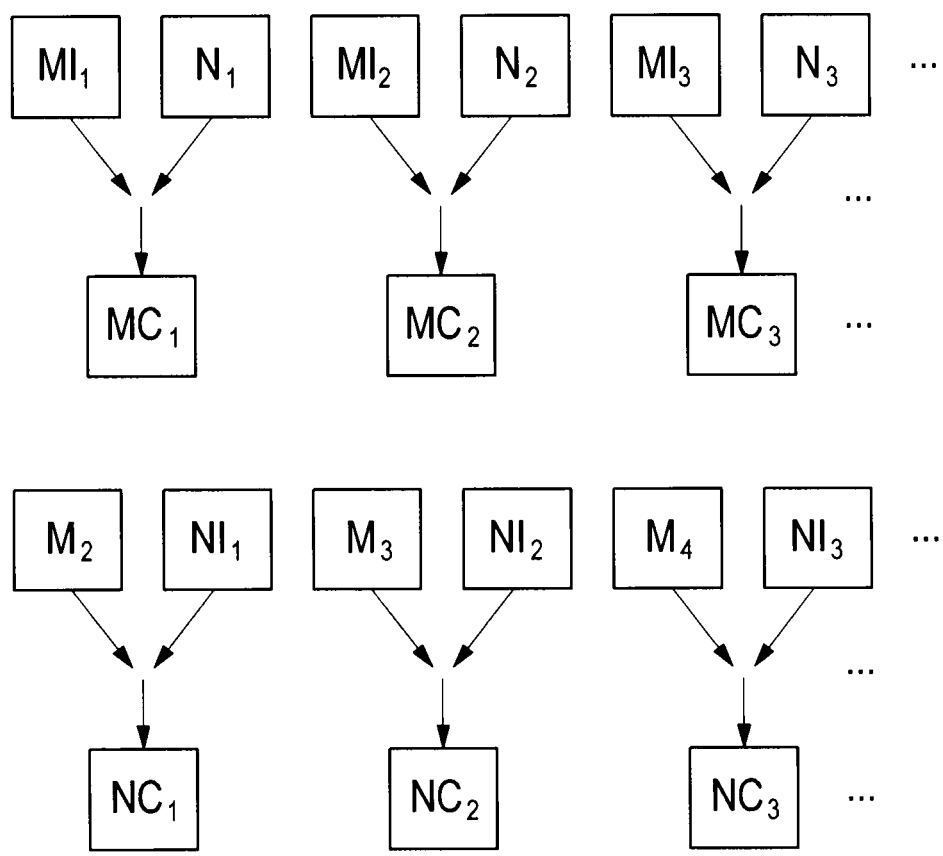
FIG. 19 is a schematic diagram showing an example of compounding reconstruction images and interpolation images.

Referring once again to FIG. 8, the image compounding unit 850 may be operable to compound an $i^{th}$ first interpolation image $MI_i$ formed in the first image processing unit 830 and an $i^{th}$ second reconstruction image $N_i$ to thereby form a compound image (hereinafter, referred to as "first compound image"). Also, the image compounding unit 850 may be further operable to compound an $(i+1)^{th}$ first reconstruction image $M_{i+1}$ formed in the first image processing unit 830 and an $i^{th}$ second interpolation image $MI_i$ to thereby form a compound image (hereinafter, referred to as "second compound image"). In one embodiment, the first and second compound images may be formed at the same time. As illustrated in FIG. 19, the image compounding unit 850 may be operable to compound the first interpolation image $MI_1$ formed in the first image processing unit 830 and the second reconstruction image $N_1$ formed in the second image processing unit 840 to thereby form the first compound image $MC_1$. In the same manner as above, the image compounding unit 850 may be operable to form a plurality of first compound images $MC_3$, . . . . Also, the image compounding unit 850 may be operable to compound the first reconstruction image $M_2$ formed in the first image processing unit 830 and the second interpolation image $NI_1$ formed in the second image processing unit 840 to thereby form the second compound image $NC_1$. In the same manner as above, the image compounding unit 850 may be operable to form a plurality of second compound images $NC_2$, $NC_3$, . . . . The image compounding unit 850 may include a first image compounding unit (not shown) for forming the first compound images and a second image compounding unit (not shown) for forming the second compound images.

Figure 20:
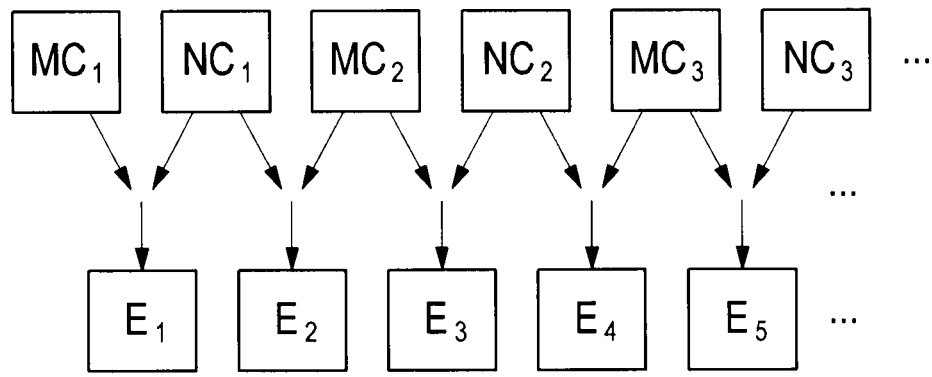
FIG. 20 is a schematic diagram showing an example of forming elastic images by using the compound images.

The ultrasound system 100 may further include an elastic image forming unit 860. The elastic image forming unit 860 may be configured to perform autocorrelation to compute an elasticity modulus between a $j^{th}$ first compound image $MC_j$ and a $j^{th}$ second compound image $NC_j$, which are formed in the image compounding unit 850, wherein j is an integer equal to or greater than 1. The elastic image forming unit 860 may be further operable to form an elastic image $E_i$ by using the computed elasticity modulus. That is, the elasticity image forming unit 860 may be configured to compute the elasticity modulus corresponding to a displacement of the blood vessel, the lipid and peripheral tissues caused by the contraction and the relaxation of the blood vessel. It may then form the elastic image based on the computed elasticity modulus. In the same manner as above, the elastic image forming unit 860 may be operable to form a plurality of elastic images $E_1$, $E_2$, $E_3$, $E_4$, $E_5$ . . . as illustrated in FIG. 20.

The ultrasound system 800 may further include a display unit 870 that may display the elastic image formed in the elastic image forming unit 860. The display unit 870 may also display the first and second ultrasound images, the first and second reconstruction images and the first and second interpolation images.

The first image processing unit 830, the second image processing unit 840, the image compounding unit 850 and the elastic image forming unit 860 of the ultrasound system 800 will be embodied with a single processor or a plurality of processors.

Third Embodiment

Figure 21:
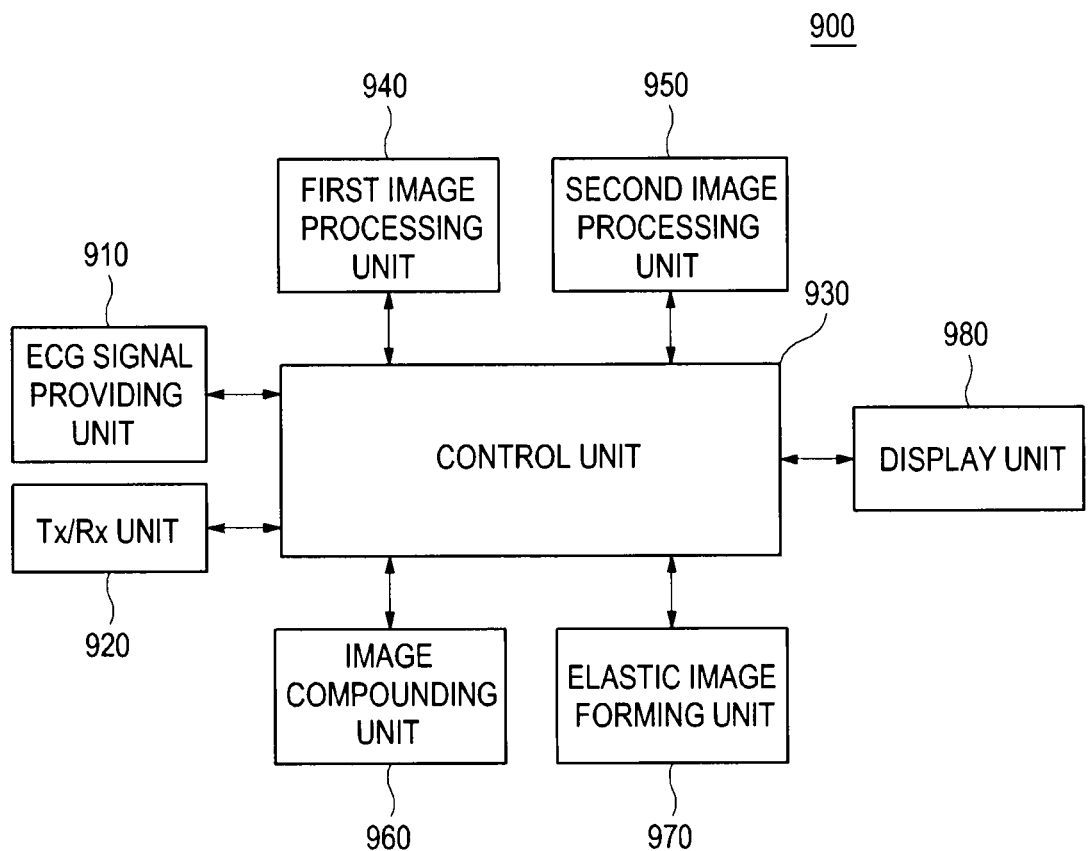
FIG. 21 is a block diagram showing an ultrasound system in accordance with a third embodiment.

FIG. 21 is a block diagram showing an illustrative embodiment of an ultrasound system. As depicted in FIG. 21, the ultrasound system 900 may further include an electrocardiogram (ECG) signal providing unit 910 compared to the ultrasound system 800 of FIG. 8. The ECG signal providing unit 910 may be configured to provide an ECG signal containing a P wave, QRS waves and a T wave. The P wave, QRS waves and T wave are well known to a person to skilled in the art. Thus, detailed descriptions thereof will be omitted herein.

The ultrasound system 900 may include a Tx/Rx unit 920. The Tx/Rx unit 920 may include a probe (not shown) for transmitting an ultrasound beam along scan lines in a target object and receiving ultrasound echoes reflected from the target object to thereby output electrical receive signals. For the sake of convenience, a blood vessel will be referred to as an example of the target object. The probe may include a linear array transducer containing a plurality of elements. The Tx/Rx unit 920 may further include a beam former for performing transmit focusing and receive focusing. In the third embodiment, the scan lines may be set to be steered. That is, the Tx/Rx unit 920 may be operable to transmit the ultrasound beam along scan lines $S_1$-$S_{11}$ ("normal scan lines") such as shown in FIG. 9 and scan lines, which are steered ("steered scan lines) $S'_1$-$S'_{11}$ such as shown in FIG. 10. The setting of the steered scan lines will be described later. The Tx/Rx unit 920 may output first electrical receive signals obtained by scanning the normal scan lines and second electrical receive signals obtained by scanning the steered scan lines. In one embodiment, the scanning of the normal scan lines may be carried out in synchronization with the P and T waves at a $(2n-1)^{th}$ cardiac cycle and the scanning of the steered scan lines may be carried out in synchronization with the P and T waves at a $(2n)^{th}$ cardiac cycle, wherein n is an integer equal to or greater than 1.

The ultrasound system 900 may further include a control unit 930 that may be operable to control the transmission and reception of the ultrasound beam. The control unit 930 may be configured to set the normal scan lines. It may also control the Tx/Rx unit 920 such that the ultrasound beam is transmitted along the normal scan lines in synchronization with the P and T waves at the $(2n-1)^{th}$ cardiac cycle. In such a case, the electrical receive signal outputted from the Tx/Rx unit 920 will be referred to as "first receive signals."

Figure 22:
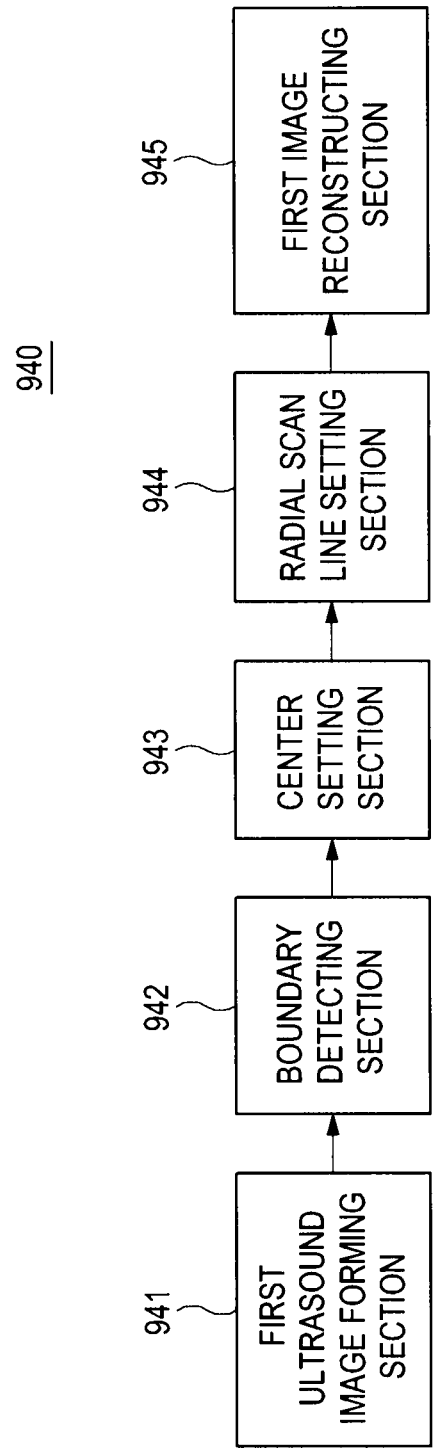
FIG. 22 is a block diagram showing a first image processing unit in accordance with the third embodiment.

The ultrasound system 900 may include a first image processing 940 that may receive the first receive signals. Referring to FIG. 22, the first image processing unit 940 may include a first ultrasound image forming section 941. The first ultrasound image forming section 941 may be operable to form a first ultrasound image based on the first receive signals such as shown in FIG. 12.

The first processing unit 940 may further include a boundary detecting section 942 that may be operable to detect boundaries of a blood vessel 212 on the first ultrasound image 210. The boundary detection may be performed similar to the boundary detection by the boundary detecting section 832 of FIG. 9. Thus, detailed descriptions of the boundary detection will be omitted herein.

The first image processing unit 940 may further include a center setting section 943. The center setting section 943 may be operable to set a center of the blood vessel by using detected boundaries. The center setting may be performed similar to the center setting by the center setting section 833 of FIG. 9. Thus, detailed descriptions of the center setting will be omitted herein.

The first image processing unit 940 may further include a radial scan line setting section 944. The radial scan line setting section 944 may be operable to set a plurality of scan lines $RS_1$-$RS_{34}$ in radial directions with respect to the center (hereinafter, referred to as "radial scan lines") on the first ultrasound image 210, as illustrated in FIG. 11. The number of the radial scan lines may be determined according to an interval of the radial scan lines, i.e., an angle, which may be set by the control unit 930. The radial scan line setting section 944 may set a plurality of sample points on each of the radial scan lines $RS_1$-$RS_{34}$ and acquire position information of the sampling points and image data at the sampling points based on the first receive signals.

The image processing unit 940 may further include a first image reconstructing section 945. The first image reconstructing section 945 may be operable to reconstruct the radial scan lines $RS_1$-$RS_{34}$ to be in parallel with each other. The first image reconstructing section 945 may be configured to form a first reconstruction image corresponding to the first ultrasound image by using the reconstructed radial scan lines $RS_1$-$RS_{34}$ and the image data of the sampling points on the radial scan lines. In one embodiment, the first image reconstructing section 945 may be operable to form the first reconstruction image by using the image data corresponding to the radial scan lines $RS_8$-$RS_{13}$ and $RS_{25}$-$RS_{30}$, which are not overlapped with the steered scan lines $S'_1$-$S'_{11}$ shown in FIG. 10.

Referring back to FIG. 21, the control unit 930 may be further operable to set the steered scan lines $S'_1$-$S'_{11}$, which are illustrated in FIG. 10, based on the center information of the blood vessel. That is, the control unit 930 may be configured to set the steered scan lines $S'_1$-$S'^{11}$ to be converged at the center of the blood vessel. The control unit 930 may control the Tx/Rx unit 920 such that the ultrasound beam is transmitted along the steered scan lines $S'_1$-$S'_{11}$ in synchronization with the P and T waves at the $2n^{th}$ cycle. In such a case, the electrical receive signal outputted from the Tx/Rx unit 920 will be referred to as "second receive signals."

Figure 23:
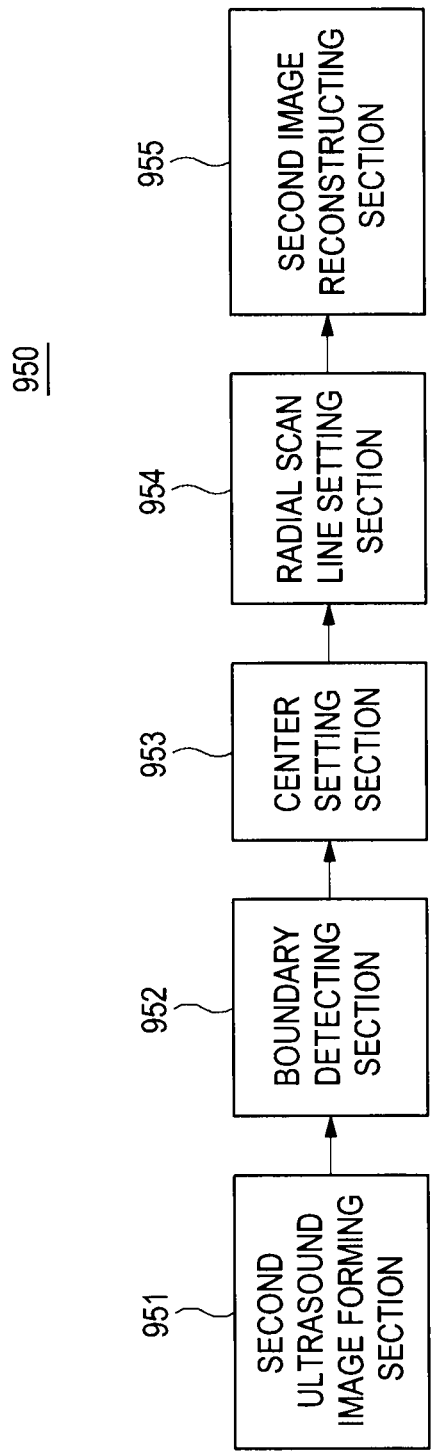
FIG. 23 is a block diagram showing a second image processing unit in accordance with the third embodiment.

The ultrasound system 900 may further include a second image processing unit 950 that may receive the second receive signals. Referring to FIG. 23, the second image processing unit 950 may include a second ultrasound image forming section 951 that may receive the second receive signals. The second ultrasound image forming section 951 may be operable to form a second ultrasound image based on the second receive signals.

The second image processing unit 950 may further include a boundary detecting section 952 that may be operable to detect boundaries of the blood vessel similar to the boundary detection in the boundary detecting section 942 of the first image processing unit 940.

The second image processing unit 950 may further include a center setting section 953. In one embodiment, the center setting section 953 may be operable to set a center of the blood vessel based on the center set by the center setting section 943 of the first image processing unit 940.

The second image processing unit 950 may further include a radial scan line setting section 954. The radial scan line setting section 954 may be operable to set a plurality of scan lines $RS_1$-$RS_{34}$ in radial directions with respect to the center (hereinafter, referred to as "radial scan lines") such as shown in FIG. 13. The number of the radial scan lines may be determined according to an interval of the radial scan lines, i.e., a steering angle, which may be set by the control unit 930. In one embodiment, the steering angle of the radial scan lines $RS_1$-$RS_{34}$ may be set to be equal to a steering angle of the steered scan lines. The radial scan line setting section 954 may set the radial scan lines $RS_1$-$RS_7$, $RS_{14}$-$RS_{24}$ and $RS_{31}$-$RS_{34}$ to be matched with the steered scan lines $S'_1$-$S'_{11}$. The radial scan line setting section 954 may set a plurality of sample points on each of the radial scan lines $RS_1$-$RS_{34}$ and acquire position information of the sampling points and image data at the sampling points based on the second receive signals.

The second image processing unit 950 may further include a second image reconstructing section 955. The second image reconstructing section 955 may be operable to reconstruct the radial scan lines $RS_1$-$RS_{34}$ to be in parallel with each other such as shown in FIG. 15. The second image reconstructing section 955 may be configured to form a second reconstruction image corresponding to the second ultrasound image by using the reconstructed radial scan lines $RS_1$-$RS_{34}$ and the image data of the sampling points on the radial scan lines. In one embodiment, the second image reconstructing section 955 may be operable to form the second reconstruction image by using the image data corresponding to the radial scan lines $RS_1$-$RS_7$, $RS_{14}$-$RS_{24}$ and $RS_{31}$-$RS_{34}$, which are overlapped with the steered scan lines $S'_1$-$S'11$ shown in FIG. 10.

Figure 24:
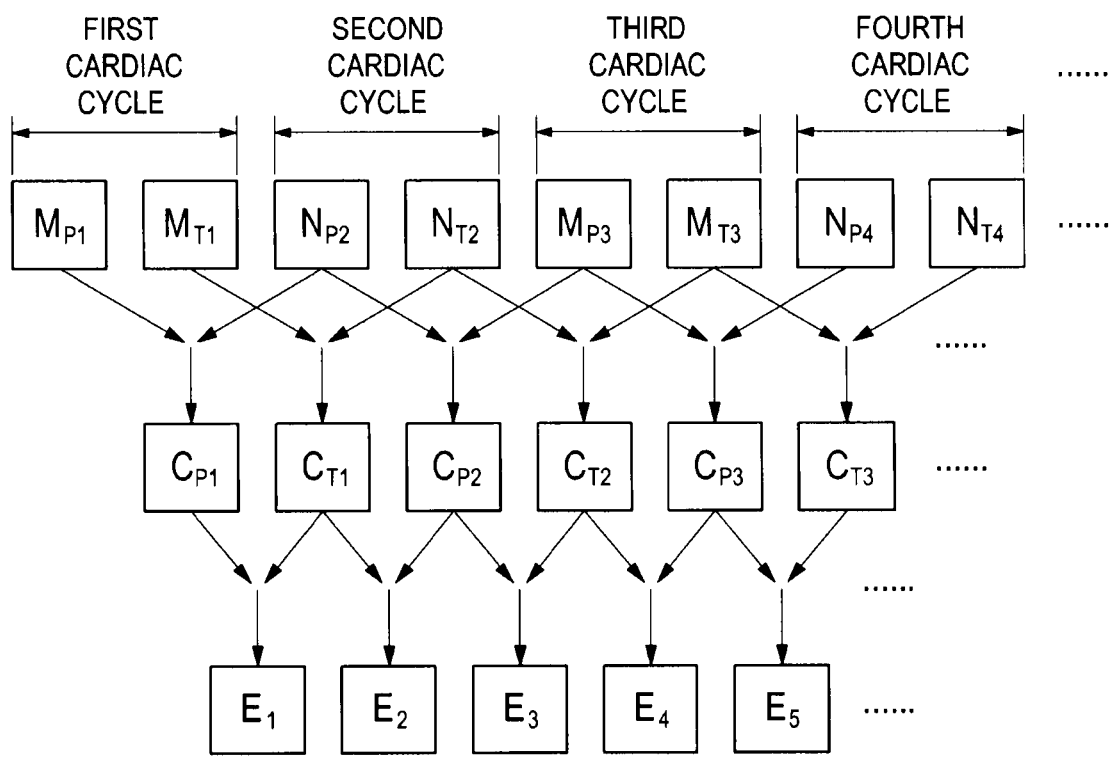
FIG. 24 is a schematic diagram showing an example of compounding ultrasound images and forming elastic images by using compound images.

Referring once again to FIG. 21, the ultrasound system 900 may further include an image compounding unit 960, which may be operable to compound the first reconstruction image formed in the first image processing unit 940 and the second reconstruction image formed in the second image processing unit 950. In such a case, the image compounding unit 960 may be configured to perform motion estimation and compensation between the first and second reconstruction images for compensating motion, which may occur in the compound image. The motion estimation and compensation may be carried out by using the well-know techniques. As such, detailed descriptions thereof will be omitted herein. The image compounding unit 960 may be operable to compound the first reconstruction image $M_{P1}$ formed in synchronization with the P wave of the first cardiac cycle and the second reconstruction image $N_{P2}$ formed in synchronization with the P wave of the second cardiac cycle to thereby form a compound image $C_{P1}$. Also, the image compounding unit 960 may be operable to compound the first reconstruction image $M_{T1}$ formed in synchronization with the T wave of the first cardiac cycle with the second reconstruction image $N_{T2}$ formed in synchronization with the T wave of the second cardiac cycle to thereby form a compound image $C_{T1}$. In the same manner as above, the image compounding unit 960 may be configured to form a plurality of compound images $C_{P2}$, $C_{T2}$, $C_{P3}$, $C_{T3}$ . . . as illustrated in FIG. 24.

Referring back to FIG. 21, the ultrasound system 900 may further include an elastic image forming unit 970. The elastic image forming unit 970 may be operable to perform autocorrelation to compute an elasticity modulus between a $k^{th}$ compound image and a $(k+1)^{th}$ compound image, which are formed in the image compounding unit 960, wherein k is an integer equal to or greater than 1. The elastic image forming unit 970 may be further operable to form an elastic image by using the computed elasticity modulus. For example, the elasticity image forming unit 970 may be operable to compute the elasticity modulus by using the first compound image $C_{P1}$ and the second compound image $C_{T1}$, and then form the elastic image $E_1$ based on the computed elasticity modulus. In the same manner as above, the elastic image forming unit 970 may be operable to form a plurality of elastic images $E_2$, $E_3$, $E_4$, $E_5$ . . . as illustrated in FIG. 24.

The ultrasound system 900 may further include a display unit 980 that may display the elastic image formed in the elastic image forming unit 970. The display unit 980 may display the first and second ultrasound images, the first and second reconstruction images and the compound images.

The first image processing unit 940, the second image processing unit 950, the image compounding unit 960 and the elastic image forming unit 970 of the ultrasound system 800 may be implemented by a single processor or a plurality of processors.

As mentioned above, the lipid or lesion at inside of the blood vessel may be examined through the elastic image without inserting the probe into the inside of the blood vessel. Also, since the ultrasound images formed in synchronization with the ECG signal are used to form the elastic image, a more accurate elastic image may be formed.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   a transmission/reception (Tx/Rx) unit configured to repeatedly transmit/receive an ultrasound beam along first scan lines and the second scan lines in a target object to output first receive signals and second receive signals, respectively, wherein the first scan lines are parallel with each other and the second scan lines are passing a center of the target object;
   an image processing unit configured to form first ultrasound images and second ultrasound images based on the first receive signals and the second receive signals, respectively, detect boundaries of the target object on each of the first ultrasound images and the second ultrasound images, and set the center of the target object on each of the first ultrasound images and the second ultrasound images based on the detected boundaries, the image processing unit being further configured to set first radial lines in first radial directions with respect to the center on each of the first ultrasound images, set second radial lines in second radial directions with respect to the center on each of the second ultrasound images, and reconstruct the first ultrasound images and the second ultrasound images such that the first radial lines and the second radial lines are in parallel with each other to form first reconstruction images and second reconstruction images, respectively;
   an image compounding unit configured to form compound images by using the first reconstruction images and the second reconstruction images; and
   an elastic image forming unit configured to form at least one elastic image based on the compound images.

2. The ultrasound system of claim 1, wherein the image processing unit includes a first image processing unit for receiving the first receive signals and a second image processing unit for receiving the second receive signals.

3. The ultrasound system of claim 2, wherein the first image processing unit includes:
   a first ultrasound image forming section for consecutively forming the first ultrasound images based on the first receive signals;
   a first boundary detecting section for detecting the boundaries of the target object on each of the first ultrasound images;
   a first center setting section for setting the center of the target object based on the detected boundaries;
   a first radial line setting section for setting the first radial lines in the first radial directions with respect to the center on each of the first ultrasound images, wherein the first radial line setting section is configured to set the first radial lines not to be matched with the second scan lines;
   a first image reconstructing section for reconstructing the first ultrasound images such that the first radial lines are in parallel with each other to form the first reconstruction images; and
   a first image interpolating section for interpolating the first reconstruction images to form first interpolation images.

4. The ultrasound system of claim 3, wherein the second image processing unit includes:
   a second ultrasound image forming section for consecutively forming the second ultrasound images based on the second receive signals;
   a second boundary detecting section for detecting the boundaries of the target object on each of the second ultrasound images;
   a second center setting section for setting the center of the target object based on the detected boundaries;
   a second radial line setting section for setting the second radial lines in the second radial directions with respect to the center on each of the second ultrasound images, wherein the second radial line setting section is configured to set the second radial lines to be matched with the second scan lines;

a second image reconstructing section for reconstructing the second ultrasound images such that the second radial lines are in parallel with each other to form the second reconstruction images; and a second image interpolating section for interpolating the second reconstruction images to form second interpolation images.

5. The ultrasound system of claim 4, wherein the image compounding unit is configured to form the compound images by using the first and second reconstruction images and the first and second interpolation images, and the image compounding unit includes:

a first image compounding section for compounding an $i^{th}$ first interpolation image and an $i^{th}$ second reconstruction image to form a first compound image, wherein i is an integer equal to or greater than 1; and a second image compounding section for compounding an $(i+1)^{th}$ first reconstruction image and an $i^{th}$ second interpolation image to form a second compound image.

6. The ultrasound system of claim 5, wherein the elastic image forming unit is configured to compute an elasticity modulus by using a $j^{th}$ first compound image and a $j^{th}$ second compound image, wherein j is an integer equal to or greater than 1.

7. The ultrasound system of claim 1, further comprising an electrocardiogram (ECG) signal providing unit configured to provide an ECG signal representing a cardiac cycle, wherein the ECG signal includes a first wave generated before contraction of a left ventricle and a second wave generated before relaxation of the left ventricle.

8. The ultrasound system of claim 7, wherein the Tx/Rx unit is configured to transmit an ultrasound beam along the first scan lines in synchronization with the first and second wave at a $(2n-1)^{th}$ cardiac cycle to thereby output first receive signals, the Tx/Rx unit being further configured to transmit an ultrasound beam along the second scan lines in synchronization with the first and second waves at a 2 nth cardiac cycle to thereby output second receive signal, wherein n is an integer equal to or greater than 1.

9. The ultrasound system of claim 8, wherein the image processing unit includes a first image processing unit for receiving the first receive signals and a second image processing unit for receiving the second receive signals.

10. The ultrasound system of claim 9, wherein the first image processing unit includes:

a first ultrasound image forming section for consecutively forming the first ultrasound images based on the first receive signals corresponding to the first and second waves, respectively, at the $(2n-1)^{th}$ cardiac cycle;

a first boundary detecting section for detecting the boundaries of the target object on each of the first ultrasound images;

a first center setting section for setting the center of the target object based on the detected boundaries;

a first radial line setting section for setting the first radial lines in the first radial directions with respect to the center on each of the first ultrasound images, wherein the first radial line setting section is configured to set the first radial lines not to be matched with the second scan lines; and a first image reconstructing section for reconstructing the first ultrasound images such that the first radial lines are in parallel with each other to form the first reconstruction images.

11. The ultrasound system of claim 10, wherein the second image processing unit includes:

a second ultrasound image forming section for consecutively forming the second ultrasound images based on the second receive signals corresponding to the first and second waves, respectively, at the $2n^{th}$ cardiac cycle;

a second boundary detecting section for detecting the boundaries of the target object on each of the second ultrasound images;

a second center setting section for setting the center of the target object based on the detected boundaries;

a second radial line setting section for setting the second radial lines in the second radial directions with respect to the center on each of the second ultrasound images, wherein the second radial line setting section is configured to set the second radial lines to be matched with the second scan lines; and a second image reconstructing section for reconstructing the second ultrasound images such that the second radial lines are in parallel with each other to form the second reconstruction images.

12. The ultrasound system of claim 10, further comprising an image compounding unit configured to compound the first reconstruction images formed in synchronization with the first wave and the second reconstruction images formed in synchronization with the first wave to output first compound images, the image compounding unit being further configured to compound the first reconstruction images formed in synchronization with the second wave and the second reconstruction images formed in synchronization with the second wave to output second compound images.

13. The ultrasound system of claim 12, wherein the elastic image forming unit is configured to compute an elasticity modulus through autocorrelation upon the first and second compound images and form elastic images by using the elasticity modulus.

14. A method of forming an elastic image in an ultrasound system including a transmission/reception (Tx/Rx) unit, an image processing unit, an image compounding unit and an elastic image forming unit, comprising:

a) using the transmission/reception (Tx/Rx) unit within the ultrasound system to repeatedly transmit/receive an ultrasound beam along first scan lines and the second scan lines in a target object to output first receive signals and second receive signals, respectively, wherein the first scan lines are parallel with each other and the second scan lines are passing a center of the target object;

b) using the image processing unit within the ultrasound system to form first ultrasound images and second ultrasound images based on the first receive signals and the second receive signals, respectively, detect boundaries of the target object on each of the first ultrasound images and the second ultrasound images, set the center of the target object on each of the first ultrasound images and the second ultrasound images based on the detected boundaries, set first radial lines in first radial directions with respect to the center on each of the first ultrasound images, set second radial lines in second radial directions with respect to the center on each of the second ultrasound images, and reconstruct the first ultrasound images and the second ultrasound images such that the first radial lines and the second radial lines are in parallel with each other to form first reconstruction images and second reconstruction images, respectively;

c) using the image compounding unit within the ultrasound system to form compound images by using the first reconstruction images and the second reconstruction images; and d) using the elastic image forming unit within the ultrasound system to form at least one elastic image based on the compound images.

15. The method of claim 14, wherein the step d) includes using the elastic image forming unit to compute an elasticity modulus between two consecutive compound images and form an elastic image based on the computed elastic modulus.

16. The method of claim 14, wherein the step a) includes using the Tx/Rx unit to transmit the ultrasound beam in synchronization with an ECG signal provided from an electrocardiogram (ECG) signal providing unit further included in the ultrasound image.

17. The method of claim 16, wherein the step b) includes using the first image processing unit to:
consecutively form the first ultrasound images based on the first receive signals;
detect the boundaries of the target object on each of the first ultrasound images;
set the center of the target object based on the detected boundaries;
set the first radial lines in the first radial directions with respect to the center on each of the first ultrasound images, wherein the first radial line setting section is configured to set the first radial lines not to be matched with the second scan lines;
reconstruct the first ultrasound images such that the first radial lines are in parallel with each other to form the first reconstruction images; and
interpolate the first reconstruction images to form the first interpolation images.

18. The method of claim 17, wherein the step b) further includes using the second image processing unit to:
consecutively form the second ultrasound images based on the second receive signals;
detect the boundaries of the target object on each of the second ultrasound images;
set the center of the target object based on the detected boundaries;
set the second radial lines in the second radial directions with respect to the center on each of the second ultrasound images, wherein the second radial line setting section is configured to set the second radial lines to be matched with the second scan lines;
reconstruct the second ultrasound images such that the second radial lines are in parallel with each other to form the second reconstruction images; and
interpolate the second reconstruction images to form the second interpolation images.

19. The method of claim 18, wherein the step c) further includes using the image compounding unit to compound an $i^{th}$ first interpolation image and an $i^{th}$ second reconstruction image to form a first compound image, wherein i is an integer equal to or greater than 1, and compound an $(i+1)^{th}$ first reconstruction image and an $i^{th}$ second interpolation image to form a second compound image.

20. The method of claim 19, wherein the step d) using the elastic image forming unit to compute an elasticity modulus by using a $j^{th}$ first compound image and a $j^{th}$ second compound image, wherein j is an integer equal to or greater than 1.

21. The ultrasound system of claim 1, wherein each reconstructed image includes a horizontal line that corresponds to the center of the target object on each respective ultrasound image, the horizontal line being perpendicular to the parallel radial scan lines, and when the target object on the ultrasound image has a shape that is substantially circular, the target object is displayed on the reconstructed image with a linear shape that is horizontally aligned with the horizontal line that corresponds to the center of the target object.

* * * * *